United States Patent [19]

Maeda et al.

[11] Patent Number: 4,880,832
[45] Date of Patent: Nov. 14, 1989

[54] LIPOSOLUBLE PLATINUM (II) COMPLEX AND PREPARATION THEREOF

[75] Inventors: Mitsuaki Maeda, Tokyo; Takuma Sasaki, Kanazawa, both of Japan

[73] Assignee: Sumitomo Pharmaceuticals Company, Ltd., Osaka, Japan

[21] Appl. No.: 156,961

[22] Filed: Feb. 18, 1988

[30] Foreign Application Priority Data

Mar. 6, 1987 [JP] Japan ................. 62-51237

[51] Int. Cl.$^4$ .............................. A61K 31/28
[52] U.S. Cl. ................... 514/492; 556/137
[58] Field of Search ............ 424/131; 556/137; 514/492

[56] References Cited

U.S. PATENT DOCUMENTS 4,452,812  6/1984  Macquet .................. 514/492

FOREIGN PATENT DOCUMENTS 0136012   3/1985   European Pat. Off. .
0193936  10/1986   European Pat. Off. .
265350A1  4/1988   European Pat. Off. .

OTHER PUBLICATIONS

Tobe and Khokhar, *J. Clin. Hematol. and Oncol.*, vol. 7, #1, pp. 113–133.

Primary Examiner—John Doll
Assistant Examiner—Stuart L. Hendrickson
Attorney, Agent, or Firm—Kerkam, Stowell, Kondracki & Clarke

[57] ABSTRACT

New delivatives of platinum (II) complex which are liposoluble and applicable as antibacterial agents or anticancer agents specific to the affected parts of patients and selectively transferred to the parts when they are used in combination with lipidol, the delivatives being represented by the general formula of:

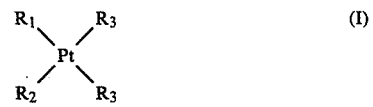

(wherein $R_1$ and $R_2$ each stands for a ligand ammine which may have an organic substituent or may be bonded to each other through a bivalent organic group and $R_3$ represents a bile acid residue). These derivatives being prepared by nitrifying a cis-dichloro-di-(substituted or unsubstituted)-ammine platinum (II) and then reacting the resulting aqua type product with a corresponding alkali metal salt of bile acid.

16 Claims, No Drawings

LIPOSOLUBLE PLATINUM (II) COMPLEX AND PREPARATION THEREOF

BACKGROUND OF THE INVENTION

1. Field of the Invention

The present invention relates to a platinum (II) complex. More particularly, the present invention pertains to a platinum (II) complex having excellent antibacterial activity and anticancer activity, in particular, effective to use as an anticancer agent and a process for preparing the same.

2. Description of the related Art

Recently, a remarkable development has been achieved in medical and pharmaceutical fields, and as a result, diseases conventionally considered to be incurable and showing a high mortality have been protected, restrained or cured (or recovered) to a substantial degree. Under such circumstances, cancer has drawn a great attention because of its high mortality. However, up to now, there has not yet been proposed an effective solution to reduce the mortality of patients suffering from cancer.

There have been proposed conventional therapeutics for cancer, such as surgical operation in which the affected part of patients is cut off, irradiation (radiotherapy), chemical therapy (chemotherapy) by administering medicines. Recently, the immunological therapy (immunotherapy), the interferon therapy, and the utilization of laser such as YAG laser as new technique of the surgical operation have drawn a great attention.

However, the surgical operation and the radiotherapy among others are a kind of locally applied techniques of therapy and are effective means for treating patients only if the disease is in its primitive state or there is not metastasis, while these therapeutics are not effective against the progressive cancer i.e., those accompanying metastasis in the whole body of patients as well as the systematic diseases such as leukemia and malignant lymphoma in which a specific system in the whole body is gradually affected. On the other hand, the chemotherapy is the only effective therapeutics against the latter systematic diseases and some of the cancer may be cured by the chemical therapy. It is also recognized that the chemotherapy is an effective tool for treating patients suffering from cancer, in particular, when it is applied as an additional or auxiliary treatment after the surgical operation or it is applied in combination with the radiotherapy and thus, this is one of the therapeutic technique in which a great future development is expected.

Up to now, various kind of anticancer agents have been developed and proposed and each of them differs in its property and the effectiveness thereof varies depending on the kind of cancer. There may be mentioned such as mitomycin C, adriamycin as the medicine against adenocarcinoma (carcinoma in digestive organs, oophoroma); vincristine, bleomycin against the malignant lymphoma; cytocine arabinoside, L-asparaginase for acute leukemia.

The chemotherapy for the cancer is based on the fact that the cancer may be caused by the parasite such as cancer cells in a human body as encountered in the case of bacteria in the general infectious diseases. In other words, the cancer cells are considered to be normal cells which are converted to a variant by some causes and the variant once formed in a body is considered to be the parasite exhibiting autonomous proliferation.

Although cancer cells and normal cells are different in their biological and biochemical properties from each other, the difference is simply in a quantitative one, while the qualitative difference between them has not yet been made clear. Therefore, the normal cells may possibly be impaired by the action of chemical agents (medicine) in the chemotherapy and this is revealed as so-called side-effects due to the medicine (such as anticancer agents). Thus, it is quite difficult to restrain only the proliferation of cancer cells or destroy only these cells utilizing such medicines.

As seen from the above, the development of a new technique for treating cancer is a principal subject to be solved in the medical and pharmaceutic fields and an absolute therapy therefor should be developed. However, it can not be expected to achieve a new drastic development in the surgical therapy and the radiotherapy. Thus, it is more preferable or practical to improve chemotherapy or to develop a new medicine since a significant future development may be expected. It is expected, in particular, as the additional or auxiliary treatment means after the surgical operation of the affected part and it may be used in combination with the radiotherapy. Furthermore, the chemotherapy may be an effective tool for treating the progressive cancer as well as the systematic diseases. Thus, there is a great need to develop a new therapeutic technique in medical or pharmaceutical science to remedy the patients suffering from these diseases. It must be said, however, that such agents should fulfill such requirement that they affect on the cancer cells specifically and selectively.

An object of this invention is to provide a novel platinum (II) complex having no side-effects which affects on cancer cells specifically and selectively.

An other object of this invention is to provide a method for preparing the platinum (II) complex.

SUMMARY OF THE INVENTION

We reviewed and made the detailed reexamination of the known platinum (II) complexes which have been utilized as anticancer agent. We had such a notion that the above mentioned problems such as side-effects may be possibly caused from their water solubility. Therefore, we thought that the platinum (II) complex which can act or affect on cancer cells specifically and selectively may be obtained if the complex is liposolubilized. Thus, we obtained different kinds of liposoluble platinum (II) complexes of the present invention.

A liposoluble platinum (II) complex according to the present invention is represented by the following formula (I):

wherein $R_1$ and $R_2$ each stands for a ligand ammine which may have an organic substituent or may be bonded to each other through a bivalent organic group and both of the $R_3$ groups are the same and individually represent a bile acid residue.

In the platinum (II) complex according to the present invention, the organic substituent in the ligand ammine substituted with organic group(s), represented by $R_1$ and $R_2$ and the bivalent organic group through which these two ammine ligands are bonded together may be those used as substituents of the ammine part ($RNH_2$) of known diammine platinum (II) complexes in the conventional anticancer agents.

Thus, the organic substituent of the ammine ligand ($R_1$ or $R_2$) may be a member selected from a group comprising an alkyl group having from 1 to 5 carbon atoms such as isopropyl group; and a cycloalkyl group having from 3 to 7 carbon atoms such as cyclopropyl group or cyclohexyl group. While, the bivalent organic group may be a member selected from the group comprising a cycloalkylene group having from 5 to 8 carbon atoms such as 1,2-cyclohexylene; an alkylene group having 2 or 3 carbon atoms, optionally substituted with an alkyl group having from 1 to 5 carbon atoms, an alkylene group having from 2 to 6 carbon atoms or a phenyl group, which includes for example groups represented by the following chemical formulae

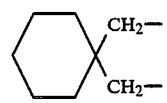

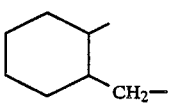

and 1,2-diphenylethylene; and 1,2-phenylene group optionally substituted with an alkyl or alkoxyl group having from 1 to 5 carbon atoms or a halogen atom such as 1,2-phenylene.

When the bivalent organic group is 1, 2-cyclohexylene or the like which possess isomers i.e., cis- DL-trans, D-trans and L-trans-form, the liposoluble platinum (II) complex according to the present invention may be any one of the isomers and a mixture thereof.

As a bile acid residue, an acyloxy part of the bile acid, which is represented by $R_3$ in the formula (I), there may be mentioned a residue of the bile acid such as cholic acids (e.g. cholic acid, deoxycholic acid, lithocholic acid, chenodeoxycholic acid, ursodeoxycholic acid, hyodeoxycholic acid) and glycyrrhizic acid.

The liposoluble platinum (II) complex of the present invention, represented by the general formula (I), can be prepared according to the following reaction scheme:

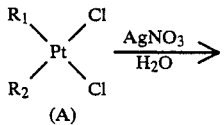

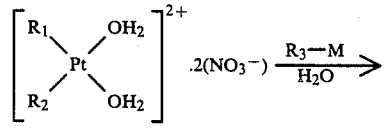

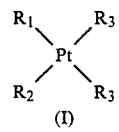

(wherein $R_1$, $R_2$ and $R_3$ are as defined above and M is an alkali metal)

According to this method, a cis-dichloro-diammine platinum (II) complex (A) is firstly converted (nitrified) to a diaquo form (B) and then the diaquo form is subjected to the reaction with a desired alkali metal salt of bile acid to produce an objective bile acid derivative of diammine platinum (II). The nitrification may be carried out by means of any conventional nitrifying agents such as silver nitrate ($AgNO_3$). As the alkali metal, in particular, sodium and potassium may be used preferably.

The reaction in which the complex (A) is converted to the diaquo form (B) of the platinum (II) complex is, in general, effected under the light-shielded condition and proceeds with high yield around room temperature. In addition, it is preferred to heat the complex (A) to a temperature of about 60° to 80 °C. prior to the addition of silver nitrate, in order to facilitate dissolution of the complex (A) into a reaction medium. The reaction time somewhat various depending on the reaction temperature, but, in general, the reaction time of about 3 hours is sufficient to achieve a good yield.

The reaction (B)→(I) is preferably carried out under the light-shielded condition as is in the reaction of (A)→(B), and is proceeded for from about 10 days to 3 weeks of the reaction time at around a room temperature.

The cis-dichloro-di-(substituted or unsubstituted)-ammine platinum (II) complexes used as a starting material in the abovementioned process can be obtained by a per se conventional method and, for instance, dichlorocyclohexane-1,2-diammine platinum (II) complex is disclosed in the article of T. A. Connors, M. Jones et al., "Chem. Biol. Interactions, 1972, 5, p415".

The platinum (II) complex of the present invention is liposoluble and has an activity to suppress the growth of the cancer cells or antibacterial activity, so that it is expected to be useful as an anticancer agent which possesses higher specificity and selectivity to the cancer cells or as an antibacterial agent. Moreover, their liposolubility makes it possible to use the complex as a medicine which can affect on the diseased part more specifically and can be released more slowly or steadily when the medicine is combined with a contrast medium as a carrier. A variety of contrast medium such as lipiodol is widely used for hepar, uterus, tuba or the like for the clinical purpose. The lipiodol is an iodinated poppy fatty acid ethyl ester and has the $I_2$ content of 38 % (w/w), the specific gravity of 1.275 to 1.290, the viscosity of 27 to 43 cS and the median lethal dose ($LD_{50}$) of 7 g/Kg when administered intravenously to rabbits. Furthermore, it is also known that the lipiodol is capable of staying stably at the vicinity of the cancer cells for a long period of time. Therefore, when the lipiodol is used in combination with the liposoluble platinum (II) complex of this invention, the anticancer agent can affect only on the cancer cell and the vicinity thereof more specifically and for longer time duration.

Further, the liposoluble platinum (II) complex of the present invention can be dispersed in physiological saline or distilled water which is then subjected to the action of ultrasonic so that micells or adequate size is formed. The resulting micell solution can be administered intravenously or into a tumor, so that it affects specifically and staidly only on the cancer cell and the vicinity thereof.

The platinum (II) complex according to the present invention may be administered in the dose of 1 mg/day to 3 g/day for an adult intravenously, orally, topically, intrarectally or intratumorally. They may be used in the form of various pharmaceutical preparations such as tablets, suppositories, injections, etc. These preparations may be formulated in per so conventional procedures. For instance, a solution or a suspension can be prepared by dissolving or dispersing the active component in a contrast medium such as lipiodol or by dispersing in an aqueous solution to form the micell according to any conventional techniques. When the lipiodol is combined with the platinum (II) complex of the present invention, it is preferable to use the platinum (II) complex in an amount ranging from 0.1 to 100 mg per 1 to 50 ml of lipiodol. These are used as a solution or a suspension as mentioned above. In the case that the platinum (II) complex of the present invention is used in the form of suspension in distilled water or physiological saline, the preferred amount ranges from 0.1 to 1 mg per 1 to 500 ml of distilled water or physiological saline.

As to cyclohexandiamine derivative of the liposoluble platinum (II) complex as the active component, it is found that it shows higher effects when it is used in the form of suspension in distilled water or in combination with lipiodol. Moreover, the use of the contrast medium makes it possible to perform the diagnosis and the therapy simultaneously so that the effectiveness of treatment for patients can be examined during the treatment.

The efficacy of the platinum (II) complex according to the invention, in particular, the anticancer activity was examined according to the folowing procedures using L 1210 -CDF1 mouse system. First of all, $1 \times 10^4$ L 1210 leukemia cells were implanted intraperitoneally to the mice and then a solution of the platinum (II) complex in 0.3 ml of lipiodol was intraperitoneally injected into the mice 24 hours and 5 days after the implantation of the leukemia cells. The platinum (II) complex was administered in three different doses as shown in the following Table I. In addition, as the controls, mice to which nothing is administered and to which only lipiodol is administered were also examined. Then, the survival time of each group of mice thus treated was determined and the mean survival time (MST) was estimated on the basis of the observed survival time of each mouse. The effectiveness of the platinum (II) complex was represented by the ratio (T/C) between the mean survival time of the mice to be treated with platinum (II) complex (T) and that of the control group of mice (C) and the ratio (CR) between the number of mice completely cured and total number of mice tested. The results obtained are listed in the following Table I.

TABLE I

Effect of the Platinum (II) Complex on the Survival Time of the CDF1 Mice Implanted with L 1210 Cells

| Compound | Dose (mg/Kg × 2) | MST | T/C | CR |
|---|---|---|---|---|
| Control | | 10 | 100 | 0/6 |
| Lipiodol | 385 | 10 | 100 | 0/6 |
| DACHPt (II)- | 1422* | — | Toxic | 1/5 |
| (Chol)$_2$ | 285 | 11.0 | 122 | 0/6 |
| | 57 | 9.0 | 100 | 0/6 |
| DACHPt (II)- | 1319 | — | Toxic | 0/6 |
| (Deoxy)$_2$ | 264 | >100 | >1000 | 5/6 |
| | 53 | 13.0 | 144 | 0/6 |
| DACHPt (II)- | 1280* | >100 | >1000 | 3/6 |
| (Litho)$_2$ | 256 | >100 | >1000 | 3/6 |
| | 51 | 11.0 | 122 | 0/6 |
| DACHPt (II)- | 793* | — | Toxic | 0/6 |
| (Urso)$_2$ | 264* | — | Toxic | 0/6 |
| | 53 | 25.5 | 283 | 2/6 |
| DACHPt (II)- | 793 | — | Toxic | 0/6 |
| (Cheno)$_2$ | 264 | — | Toxic | 0/6 |
| | 53 | 19.0 | 190 | 1/6 |

*In these samples, the platinum (II) complex was administered only one time.
DACH: Cyclohexane-1,2-diammine
Chol: Cholic acid residue (OCOC$_{23}$H$_{39}$O$_3$)
Deoxy: Deoxycholic acid residue (OCOC$_{23}$H$_{39}$O$_2$)
Litho: Lithocholic acid residue (OCOC$_{23}$H$_{39}$O)
Urso: Ursodexycholic acid residue (OCOC$_{23}$H$_{39}$O$_2$)
Cheno: Chenodeoxycholic acid residue (OCOC$_{23}$H$_{39}$O$_2$)

In the results shown in Table I, MST and T/C for the control group and the group to which lipiodol was administered were given 10.0 and 100 respectively and these values were adopted as the standard. It is the matter of course that CR was 0 in these cases. As to the groups to which the liposoluble platinum (II) complex according to the present invention is administered, it is observed that mice are sacrificed due to the toxicity of the platinum (II) complex if it was administered in a high dose, however, excellent results were obtained when the complexes were applied in relatively low dose. In particular, the group of mice to which the deoxycholic acid derivative was administered in the amount of 264 mg/kg shows the value of complete cure ratio (CR) of 5/6, the group administered lithocholic acid derivative in the amount of 1280 mg/kg and 256 mg/kg shows that of 3/6; the group to which 53 mg/kg of the ursodeoxycholic acid derivative is administered shows that of 2/6; that of the group to which 53 mg/kg of the chenodeoxychloic acid derivative is administered is 1/6.

Further, the anticancer activity of the platinum (II) complex according to the present invention was examined according to the same procedures as the above mentioned examples for L 1210-CDF$_1$ mouse system. Namely, $1 \times 10^4$ of L 1210 leukemia cells were implanted intraperitoneally to the mice and then a suspension of the platinum (II) complex in 0.3 ml of distilled water which was treated previously by ultrasonic was intraperitoneally injected. The platinum (II) complex was administered in three different doses as shown in the following Table II. In addition, as the controls, mice to which nothing is administered were also examined. Then, the survival time of each group of mice thus treated was determined and the mean survival time (MST), the ratio of prolongation of life (T/C) and the complete cure ratio (CR) were estimated on the basis of the observed survival time of each mouse. The obtained results are shown in the following Table II.

TABLE II

Effect of the Platinum (II) Complex on the Survival Time of the CDF₁ Mice Implanted with L 1210 Cells

| Compound | Dose (mg/Kg × 2) | MST | T/C | CR |
|---|---|---|---|---|
| Control | | 10 | 100 | 0/6 |
| DACHPt (II)-(Chol)₂ | 792 | >120 | >1200 | 3/6 |
| | 264 | 17.5 | 194 | 1/6 |
| | 53 | 14.0 | 140 | 0/6 |
| DACHPt (II)-(Deoxy)₂ | 854 | — | Toxic | 0/6 |
| | 285 | >120 | >1200 | 4/6 |
| | 57 | 18.5 | 206 | 2/6 |
| DACHPt (II)-(Litho)₂ | 791* | 9.5 | 106 | 0/6 |
| | 264 | >90 | >900 | 5/6 |
| | 53 | 21.0 | 210 | 2/6 |
| DACHPt (II)-(Urso)₂ | 791* | — | Toxic | 0/6 |
| | 264 | — | Toxic | 0/6 |
| | 88 | >90 | >900 | 5/6 |
| DACHPt (II)-(Cheno)₂ | 791* | — | Toxic | 0/6 |
| | 264 | — | Toxic | 0/6 |
| | 88 | >90 | >900 | 4/6 |

*In these samples, the platinum (II) complex was administered only one time.

In Table II, MST and T/C for the control group were given 10.0 and 100 respectively and these values were adopted as the standards. It is the matter of course that CR was 0 in these cases. As to the groups to which the liposoluble platinum (II) complex according to the present invention is administered, it is observed that mice are sacrificed due to the toxicity of the platinum (II) complex when they was administered in a high dose, however, excellent results were obtained when the complexes were applied in relatively low dose.

In particular, the group of mice to which the cholic acid derivative was administered in the amount of 792 mg/kg shows the CR value of 3/6, the group administered deoxycholic acid derivative in the amount of 285 mg/kg shows that of 4/6; the group to which 264 mg/kg of the lithocholic acid derivative is administered shows that of 5/6; that of the group to which 88 mg/kg of the ursodeoxycholic acid derivative is administered show that of 5/6; that of the group to which 88 mg/kg of the chenodeoxycholic acid derivative is administered shows that of 4/6.

Thus, according to the present invention, it is possible to provide a new platinum (II) complex which has an excellent liposolubility and which is applicable as anticancer agent or antimicrobial agent. In general, it is usual requirement for not only anticancer agents but also for other medicines that medicines must have such properties that they affect specifically on the deseased part and they do not impair normal cells. Since the platinum (II) complex of the present invention is liposoluble, they can be expected to have a high specificity to affected portions. Moreover, if the lipiodol which is capable of staying preferentially at the vicinity of the cancer cells for a long period of time is used in combination with the liposoluble platinum (II) complex of this invention, or if the platinum (II) complex is dispersed in distilled water or physiological saline in the form of suspension which is subjected to the ultrasonic-treatment in order to form micells, it is possible to obtain the anticancer agents which have the excellent specificity and which can be carried specifically to the cancer cells or the vicinity thereof and can be released slowly and can keep steady and long-lasting effects. Namely, the present invention provides very useful anticancer agents having a high specificity and selectivity with little side-effects such as nephrotoxicity of the conventional cysplatine.

The present invention will be explained in more detail, by the following illustrative examples which are not limitative.

EXAMPLE 1

Synthesis of Cyclohexane-1, 2-diammine Platinum (II) Bischolate

Starting from cyclohexane-1, 2-diammine consisting of about 65 % of trans-isomer and about 35 % of cis-isomer, dichlorocyclohexane-1, 2-diammine platinum (II) complex was prepared according to the method disclosed in Chem. Biol. Interactions, 1972, 5, p415. A mixture of 80 ml of distilled water and 570 mg (1.5 mmoles) of dichlorocyclohexanee-1, 2-diammine platinum (II) complex was allowed to heat to 70 ° C. to dissolve most of the complex. To the solution, after being cooled to room temperature, an aqueous solution of 510 mg (3 mmoles) of silver nitrate in 10 ml of water was added and the mixture was stirred for three hours under light shielded condition. The resulting silver chloride was then filtered off and washed over CELITE. The combined filtrate was concentrated to a volume of less than 50 ml at a temperature of lower than 30 ° C. The resultant concentrate was used in the subsequent reaction.

Thus, an aqueous solution of the complex in the aqua form obtained was added to 50 ml of aqueous suspension which was prepared by dispersing 1.29 g (3 mmoles) of sodium choleate into water. The reaction was carried out under stirring and the light shielded condition for 10 days, the resulting milky white suspension was freeze-dried as it is given the objective platinum (II) complex.

Rf [Silica gel TLC, $CHCl_3$-MeOH (4:1)]0.41 (cis), 0.20 (trans).

I. R. (cm−1): 3350 (s, b), 2900 (m), 2840 (m), 1550 (m), 1370 (vs), 1070 (w), 1030 (w), 975 (w).

EXAMPLE 2

The procedure of the Example 1 were repeated except that as the alkali salt of bile acid, sodium deoxycholate, sodium lithocholate, sodium chenodeoxycholate, sodium ursodeoxycholate or sodium hyodeoxycholate were used instead of sodium cholate and thus the following compounds were prepared:

*DACHPt (II) (Deoxy)2:

Rf [Silica gel TLC, $CHCl_3$-MeOH (4:1)]0.66 (trans), 0.55 (cis).

I. R. (cm−1): 3350 (s, b), 2900 (m), 2840 (m), 1550 (m), 1380 (vs), 1030 (w).

*DACHPt (II) (Litho)2:

Rf [Silica gel TLC, $CHCl_3$-MeOH (4:1)]0.92 (cis), 0.87 (trans).

I. R. (cm−1): 3380 (s, b), 2920 (m), 2850 (m), 1560 (m), 1390 (vs), 1030 (w).

*DACHPt (II) (Cheno)2:

Rf [Silica gel TLC, $CHCl_3$-MeOH (4:1)]0.75 (trans), 0.61 (cis).

I. R. (cm−1): 3360 (s, b), 2910 (m), 2850 (m), 1555 (m), 1370 (vs), 1075 (w), 975 (w), 835 (vw).

*DACHPt (II) (Urso)2:

Rf [Silica gel TLC, $CHCl_3$-MeOH (4:1)] 0.77 (trans), 0.66 (cis).

I. R. (cm−1) 3360 (s, b), 2920 (m), 2850 (m), 1560 (m), 1380 (vs), 1040 (w), 1010 (W).

*DACHPt (II) (Hyo)2:
('Hyo' is hyodeoxycholic acid residue (OCOC$_{23}$H$_{40}$O$_2$))
Rf [Silica gel TLC, CHCl$_3$-MeOH (4:1)]; 0.66 (trans), 0.61 (cis).
I. R. (cm$^{-1}$): 3360 (s, b), 2920 (m), 2850 (m), 1560 (m), 1380 (vs), 1030 (w), 830 (vw).

What is claimed is:

1. A platinum (II) complex represented by the formula (I):

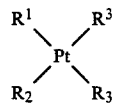

(I)

wherein R$^1$ and R$^2$ each stands for a ligand ammine which may have an organic substituent or may be bonded to each other through a bivalent organic group and both of the R$_3$ groups are the same and individually represent a residue of a bile acid selected from the group consisting of cholic acid, deoxycholic acid, lithocholic acid, chenodeoxycholic acid, ursodeoxycholic acid and hyodeoxycholic acid.

2. A platinum (II) complex as set forth in claim 1, wherein said organic substituent of the ligand ammine is an alkyl group having from 1 to 5 carbon atoms or a cycloalkyl group having from 3 to 7 carbon atoms.

3. A platinum (II) complex as set forth in claim 1, wherein said bivalent organic group is a member selected from the group consisting of a cycloalkylene group having from 5 to 8 carbon atoms; an alkylene group having from 2 or 3 carbon atoms, unsubstituted or substituted with an alkyl group having from 1 to 5 carbon atoms, an alkylene group having from 2 to 6 carbon atoms or a phenyl group; and 1,2-phenylene group unsubstituted or substituted with an alkyl or alkoxyl group having from 1 to 5 carbon atoms or a halogen atom.

4. A platinum (II) complex as set forth in claim 1, wherein R$_1$ and R$_2$ are unsubstituted ammines.

5. A platinum (II) complex as set forth in claim 1 wherein R1 and R2 are ligand ammines bonded to each other through a bivalent organic group.

6. A platinum (II) complex as set forth in claim 5 wherein the bivalent organic group is 1, 2-cyclohexylene group.

7. Cyclohexane-1, 2-diammine platinum (II) bischolate.

8. Cyclohexane-1, 2-diammine platinum (II) bisdeoxycholate.

9. Cyclohexane-1, 2-diammine platinum (II) bislithocholate.

10. Cyclohexane-1, 2-diammine platinum (II) bischenodeoxycholate.

11. Cyclohexane-1, 2-diammine platinum (II) bisursodeoxycholate.

12. Cyclohexane-1, 2-diammine platinum (II) bishyodeoxycholate.

13. A pharmaceutical composition useful for the treatment of tumor cells sensitive to a platinum complex of claim 1 which comprises an effective amount of a platinum (II) complex of claim 1 as an active ingredient and a pharmaceutically acceptable carrier or diluent therefor.

14. A method of treating tumor cells sensitive to a platinum complex of claim 1 which comprises administering an effective amount of a platinum (II) complex of claim 1 to a patient.

15. A method as set forth in claim 14 wherein said platinum (II) complex is incorporated in a lipiodol as a carrier or diluent.

16. A method of suppressing the proliferation of the cancer cells which comprises treating the cells with an effective amount of a platinum (II) complex of claim 1.

UNITED STATES PATENT AND TRADEMARK OFFICE
CERTIFICATE OF CORRECTION

PATENT NO. : 4,880,832

DATED : November 14, 1989

INVENTOR(S) : Mitsuaki MAEDA, ET AL

It is certified that error appears in the above-identified patent and that said Letters Patent is hereby corrected as shown below:

On the face of the patent, in column 1 thereof, line 1 of the Abstract, delete "(IT)" and substitute therefor -- (II) --.

Signed and Sealed this

Twenty-second Day of January, 1991

Attest:

HARRY F. MANBECK, JR.

*Attesting Officer*     *Commissioner of Patents and Trademarks*